US010335274B2

(12) United States Patent
Carpentier et al.

(10) Patent No.: US 10,335,274 B2
(45) Date of Patent: Jul. 2, 2019

(54) ERGONOMIC MITRAL HEART VALVE HOLDERS

(71) Applicant: Edwards Lifesciences Corporation, Irvine, CA (US)

(72) Inventors: Alain F. Carpentier, Paris (FR); Michael C. Murad, Tustin, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 742 days.

(21) Appl. No.: 14/797,110

(22) Filed: Jul. 11, 2015

(65) Prior Publication Data

US 2015/0313712 A1 Nov. 5, 2015

Related U.S. Application Data

(62) Division of application No. 13/306,212, filed on Nov. 29, 2011, now Pat. No. 9,078,750.

(60) Provisional application No. 61/418,182, filed on Nov. 30, 2010.

(51) Int. Cl.
*A61F 2/24* (2006.01)
*A61B 17/00* (2006.01)
*A61B 17/04* (2006.01)

(52) U.S. Cl.
CPC .............. *A61F 2/2427* (2013.01); *A61F 2/24* (2013.01); *A61B 2017/00243* (2013.01); *A61B 2017/0496* (2013.01); *A61F 2/2409* (2013.01); *A61F 2/2454* (2013.01); *A61F 2230/0071* (2013.01)

(58) Field of Classification Search
CPC ........ A61F 2/2427; A61F 2/24; A61F 2/2454; A61F 2230/0071; A61F 2/2409; A61F 2/2412; A61F 2/2439; A61B 2017/00243; A61B 2017/0496
See application file for complete search history.

(56) References Cited

U.S. PATENT DOCUMENTS

| | | | |
|---|---|---|---|
| 4,865,600 A * | 9/1989 | Carpentier | A61F 2/2427 623/2.11 |
| 5,403,305 A * | 4/1995 | Sauter | A61B 17/00234 606/1 |
| 5,855,602 A * | 1/1999 | Angell | A61F 2/2409 606/1 |
| 5,861,028 A | 1/1999 | Angell | |

(Continued)

*Primary Examiner* — Ryan J. Severson
(74) *Attorney, Agent, or Firm* — Guy Cumberbatch (57) ABSTRACT

A holder for a prosthetic mitral heart valve that attaches to an inflow end of the valve and includes a simple tensioning mechanism that flexes the heart valve commissure posts inward to help prevent suture looping. The tensioning mechanism may include relatively movable rings of the holder or a generally unitary holder with a tensor, or rotatable knob. Connecting sutures thread through internal passages in the holder and travel in the outflow direction along valve commissure posts, emerging at the post tips and mutually crossing over the outflow side of the valve. A handle attaches off-center on the holder to increase visualization of and access to the heart valve through a central window for enhanced access to the commissure posts and leaflets. The holder is constructed of non-metallic materials so as to avoid interfering with imaging devices, and the handle is ergonomically curved and shaped to facilitate manipulation.

23 Claims, 4 Drawing Sheets

(56) References Cited

U.S. PATENT DOCUMENTS

| | | | | |
|---|---|---|---|---|
| 6,090,138 | A * | 7/2000 | Chasak | A61F 2/2427 606/1 |
| 6,126,007 | A * | 10/2000 | Kari | A61F 2/0095 206/363 |
| 6,409,758 | B2 * | 6/2002 | Stobie | A61F 2/2427 606/108 |
| 6,702,852 | B2 * | 3/2004 | Stobie | A61F 2/2427 606/108 |
| 6,964,682 | B2 * | 11/2005 | Nguyen-Thien-Nhon | A61F 2/2427 623/2.11 |
| 6,966,925 | B2 * | 11/2005 | Stobie | A61F 2/2427 623/2.11 |
| 7,018,407 | B1 * | 3/2006 | Wright | A61F 2/2427 623/2.11 |
| 7,033,390 | B2 * | 4/2006 | Johnson | A61F 2/2412 623/2.11 |
| 7,189,258 | B2 * | 3/2007 | Johnson | A61F 2/2412 623/2.11 |
| 7,468,073 | B2 * | 12/2008 | Johnson | A61F 2/2412 623/2.11 |
| 7,503,929 | B2 * | 3/2009 | Johnson | A61F 2/2412 623/2.11 |
| 7,658,763 | B2 * | 2/2010 | Stobie | A61F 2/2427 623/2.11 |
| 7,819,915 | B2 * | 10/2010 | Stobie | A61F 2/2427 623/2.11 |
| RE42,395 | E * | 5/2011 | Wright | A61F 2/2427 623/2.11 |
| 8,267,993 | B2 * | 9/2012 | Nguyen | A61F 2/2445 623/2.11 |
| 8,348,998 | B2 * | 1/2013 | Pintor | A61F 2/2409 623/2.11 |
| 9,078,750 | B2 * | 7/2015 | Carpentier | A61F 2/24 |
| 9,289,293 | B2 * | 3/2016 | Murad | A61F 2/0095 |
| RE46,668 | E * | 1/2018 | Stobie | |
| 9,861,478 | B2 * | 1/2018 | Murad | A61F 2/0095 |
| RE47,065 | E * | 10/2018 | Stobie | A61F 2/2427 |
| 2002/0013621 | A1 * | 1/2002 | Stobie | A61F 2/2427 623/2.11 |
| 2004/0024451 | A1 * | 2/2004 | Johnson | A61F 2/2412 623/2.11 |
| 2004/0138741 | A1 * | 7/2004 | Stobie | A61F 2/2427 623/2.11 |
| 2004/0148017 | A1 | 7/2004 | Stobie | |
| 2005/0251252 | A1 * | 11/2005 | Stobie | A61F 2/2427 623/2.11 |
| 2006/0282162 | A1 * | 12/2006 | Nguyen | A61F 2/2445 623/2.11 |
| 2009/0259305 | A1 * | 10/2009 | Lane | A61F 2/2427 623/2.11 |
| 2010/0331972 | A1 * | 12/2010 | Pintor | A61F 2/2409 623/2.11 |
| 2012/0136434 | A1 * | 5/2012 | Carpentier | A61F 2/2427 623/2.11 |
| 2015/0313712 | A1 * | 11/2015 | Carpentier | A61F 2/2427 623/2.11 |

* cited by examiner

*Fig. 7* ized holder attaches to an inflow end of the valve

ERGONOMIC MITRAL HEART VALVE HOLDERS

RELATED APPLICATIONS

The present application is a divisional of U.S. Ser. No. 13/306,212, filed Nov. 29, 2011, now U.S. Pat. No. 9,078,750, which in turn claims priority under 35 U.S.C. § 119 to U.S. Provisional Application No. 61/418,182 filed on Nov. 30, 2010, the entire disclosures which are incorporated by reference herein.

FIELD OF THE INVENTION

The present invention relates to a device for delivering an implant and, more particularly, to a handle and holder for delivering and facilitating implant of a mitral prosthetic heart valve.

BACKGROUND OF THE INVENTION

In mammalian animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves, and each has leaflets to control the directional flow of blood through the heart. The valves are each supported by an annulus that comprises a dense fibrous ring attached either directly or indirectly to the atrial or ventricular muscle fibers. Various surgical techniques may be used to repair a diseased or damaged valve. In a valve replacement operation, the damaged leaflets are excised and the annulus sculpted to receive a replacement valve, or in some cases the valve implants over the native leaflets.

Heart valve prostheses are either of the mechanical type that uses a ball and cage or a pivoting mechanical closure, or a tissue type or "bioprosthetic" valve typically constructed with natural-tissue valve leaflets. In bioprosthetic valves the leaflets function much like in a natural human heart valve; imitating the action of the natural leaflets to coapt against each other and ensure one-way blood flow. A whole xenograft valve (e.g., porcine) or a plurality of xenograft leaflets (e.g., bovine pericardium) provide occluding surfaces that are mounted within a surrounding stent structure, typically having commissure posts extending downstream or in the outflow direction. Research is ongoing on synthesizing the tissue leaflets, and therefore the term "flexible leaflet valve" may refer to both bioprosthetic and artificial valves. In both types of prosthetic valves, a biocompatible cloth-covered suture or sewing ring is provided, on the valve body for the mechanical type of prosthetic valve, or on the inflow end of the stent for the tissue-type of prosthetic valve.

When placing a flexible leaflet prosthetic valve in the mitral position, the commissure posts are on the leading or blind side of the valve during delivery and implant, and the surgeon advances the valve down a parachute array of sutures that are pre-installed in the mitral annulus. The difficulty of the delivery task is compounded by the small access pathway into the left atrium. Suture looping sometimes occurs when one or more of the sutures in the parachute array inadvertently wraps around the inside of one or more of the commissure post tips. If this occurs, the looped suture(s) may slow down the implant procedure, damage one of the tissue leaflets when tightly tied down, or interfere with valve operation and prevent maximum coaptation of the valve leaflets, resulting in a deficiency in the prosthetic mitral valve.

One of the functions of many mitral tissue valve holders is to mitigate the potential for suture looping of the struts and/or cords during implantation. Existing devices on the market attempt to achieve this by moving the commissure struts toward the central axis of the valve (strut binding). For example, U.S. Pat. No. 4,865,600 to Carpentier, et al., provides a holder having a mechanism that constricts the commissure posts inwardly prior to implantation. The Carpentier device provides an elongate handle to both hold the valve/valve holder combination during implantation, as well as to cause the commissure posts to constrict inwardly. More recently, U.S. Pat. Nos. 6,409,758, 6,702,852, 6,964,682, 6,966,925, and 7,033,390 disclose heart valve holder systems that resist suture looping.

SUMMARY OF THE INVENTION

A more ergonomic holder for a prosthetic mitral heart valve disclosed herein attaches to an inflow end of the valve and includes a simple tensioning mechanism that flexes the heart valve commissure posts inward to help prevent suture looping. The tensioning mechanism may include relatively movable rings of the holder or a generally unitary holder with a tensor, or rotatable knob. A handle desirably attaches off-center on the holder to increase visualization of and access to the heart valve through a central window. The handle is ergonomically curved and shaped to facilitate manipulation. The holder desirably has an open inner diameter for enhanced access to the commissure posts and leaflets.

Embodiments of the present application include a holder for handling and delivering a prosthetic mitral heart valve to an implantation site, the valve having an inflow end and three flexible commissures ending in tips projecting in an outflow direction.

In one combination of holder and valve, the holder has a holder body contacting the inflow end of the heart valve, the holder body defining a central window through which leaflets of the valve are visible and having internal peripheral passages. Three connecting sutures each fixed to the holder body and having a loop extending through the internal peripheral passages, out of the holder body and along each of the commissure posts of the valve. The three closed ends of the loops of the connecting sutures mutually crossing over between the tips of the commissure posts. A tensioning mechanism on the holder applies tension to the connecting sutures to cause the commissure post tips to move radially inward. A handle desirably attaches adjacent a peripheral edge of the holder and angles radially outward therefrom.

In another combination holder and valve, the holder body contacts the inflow end of the heart valve, and the holder body defining a central window through which leaflets of the valve are visible. Connecting sutures are each fixed to the holder body and extend from the holder body along each of the commissure posts of the valve, the connecting sutures crossing between the tips of the commissure posts. A tensioning mechanism on the holder applies tension to the connecting sutures to cause the commissure post tips to move radially inward, and a handle attaches adjacent a peripheral edge of the holder and angles radially outward therefrom.

In either of the preceding combinations, the tensioning mechanism on the holder may be a rotatable tensor operable from an inflow side of the holder and connected to a spool around which is wrapped each of the connecting sutures so that rotation of the tensor applies tension to the connecting sutures. The tensor may be a separate element adjacent the handle, or the handle may be the tensor and is rotatable relative to the holder body. Alternatively, the holder body has relatively rotatable rings, and each connecting suture has two free ends attached to different rotatable rings and the loop, wherein relative rotation of the rings applies tension to the connecting sutures. The relatively rotatable rings may have engaging ratchet teeth to permit relative rotation in one direction only, and a pair of steps that engage to limit total relative rotation. The handle preferably angles outward in an S-shape, such a first portion that angles outward initially between 5°-20° and a second portion that angles outward between about 20°-60°.

A further combination of a holder for handling and delivering a prosthetic mitral heart valve to an implantation site, comprises a prosthetic mitral heart valve having an inflow end and three flexible commissures ending in tips projecting in an outflow direction, the heart valve defining a flow orifice having a nominal size in millimeters corresponding to a labeled size. A holder body contacts the inflow end of the heart valve and defines a large central window through which leaflets of the valve are visible, the central window having a diameter approximately the same as the valve size. Connecting sutures each fix to the holder body and connect the valve to the holder. A handle attached adjacent a peripheral edge of the holder angles radially outward therefrom. The handle may angle outward in an S-shape, and preferably has a first portion that angles outward initially between 5°-20° and a second portion that angles outward between about 20°-60°. A tensioning mechanism may be provided on the holder to apply tension to the connecting sutures to cause the commissure post tips to move radially inward. The tensioning mechanism may be a rotatable tensor operable from an inflow side of the holder and connected to a spool around which is wrapped each of the connecting sutures so that rotation of the tensor applies tension to the connecting sutures. The tensor may comprise a separate element adjacent the handle, or the tensor comprises the handle which is rotatable relative to the holder body. A tensioning mechanism may be provided on the holder to apply tension to the connecting sutures and cause the commissure post tips to move radially inward, wherein the holder body has relatively rotatable rings, and each connecting suture has two free ends attached to different rotatable rings and a loop therebetween that passes through the valve and across the commissure post tips, wherein relative rotation of the rings applies tension to the connecting sutures.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

A prosthetic mitral heart valve holder disclosed herein includes a mechanism that pulls the heart valve commissure posts inward to help prevent suture looping. In contrast with earlier devices, the mechanism is relatively simple. In addition, the handle for the holder attaches off-center to increase visualization of and access to the heart valve through the center of the holder. Moreover, the holder and handle are constructed of non-metallic materials so as to avoid interfering with imaging devices. It should be understood that each of these benefits may be implemented on their own, or in combination with one or more of the others.

A preferred embodiment of the prosthetic heart valve holder disclosed herein includes a ring that attaches to the inflow side of the sewing ring, as shown in the attached drawings. Preferably, the inner diameter of the ring remains open, allowing access to the struts and leaflets. A curved handle attaches to the ring above one of the valve commissures. In one embodiment, at the location of the handle, a "tensor" separate from the handle connects to a ratcheting mechanism that causes commissure posts of the prosthetic heart valve to bend inward when the tensor is rotated. In an alternate embodiment, the handle is attached by way of the tensor (the handle is the tensor) such that rotation of the handle causes rotation of the tensor and thus flexing and constriction of the commissure posts.

Figure 1:
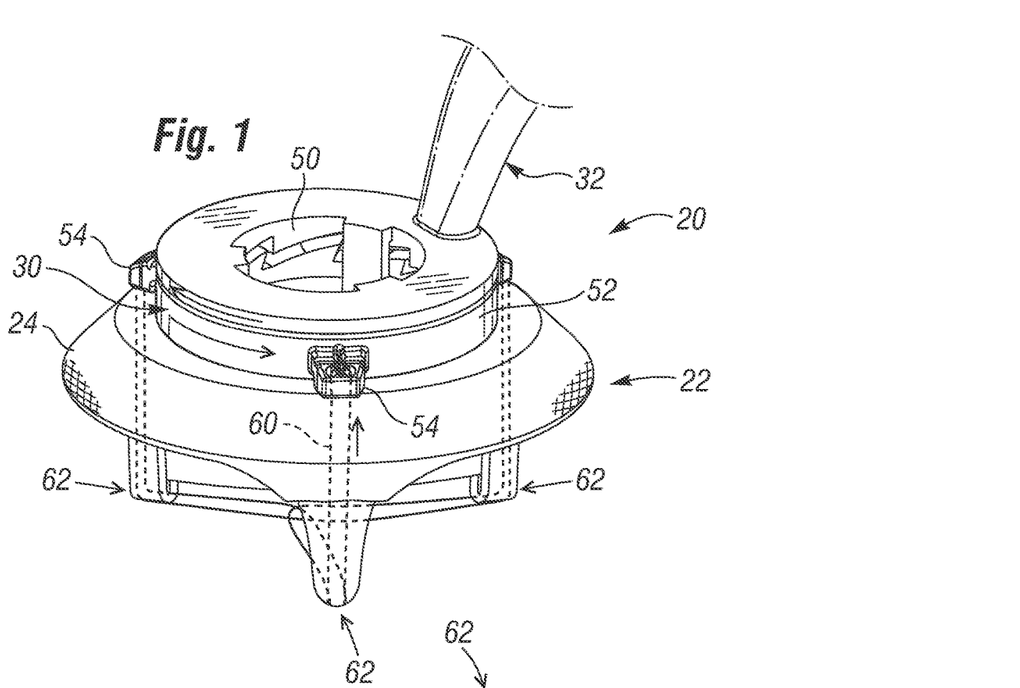
FIG. 1 is a perspective view of an exemplary holder attached to a prosthetic heart valve as seen from an inflow side, illustrating the distal end of an offset ergonomic handle.
Figure 2:
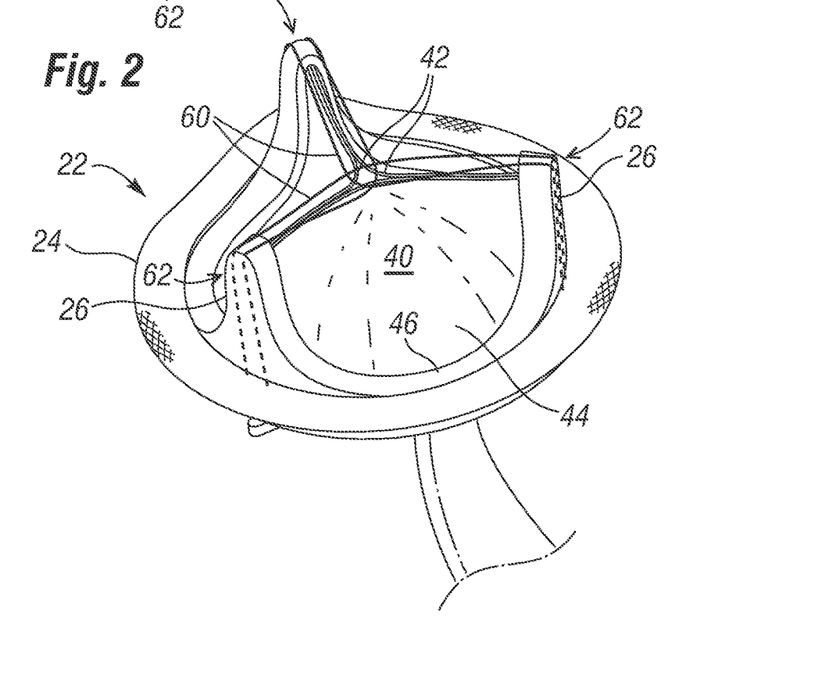
FIG. 2 is a perspective view of the assembled holder and prosthetic heart valve of FIG. 1 shown from an outflow side of the valve.

FIGS. 1 and 2 are perspective views of an exemplary holder 20 attached to a prosthetic mitral heart valve 22. Because of the position of the mitral annulus, prosthetic mitral heart valves are delivered outflow side first through the left atrium. The prosthetic heart valve 22 therefore includes a sewing ring 24 on an inflow side, and a plurality of commissure posts 26 extending in the outflow direction. The holder 20 includes a peripheral ring or body 30 that abuts the heart valve sewing ring 24, and a handle 32 more completely shown in FIGS. 3 and 4. As mentioned, the holder 20 is preferably constructed of non-metallic materials such as polypropylene or other inert material which can be molded or machined to the desired configuration. Preferably the materials are inexpensive and the holder 20 can economically be disposed of after a single use, especially as the holder is typically secured to the heart valve at the time of manufacture, though it is also conceivable to sterilize the holder for multiple uses.

The heart valve 22 as seen in FIG. 2 comprises a plurality of flexible leaflets 40 supported by the commissure posts 26. More particularly, each leaflet 40 includes a free edge 42 that extends between two of the commissure posts 26, and a cusp edge 44 that connects to structure within the commissure posts and within cusp regions 46 of the heart valve.

The illustrated valve 22 is representative of a number of mitral heart valves that may benefit from various aspects described herein. For example, prosthetic heart valves that have flexible leaflets, such as those shown at 40 in FIG. 2, typically provide commissure posts between which the leaflets are supported. The commissure posts extend in the outflow direction and therefore sometimes become entangled with a parachute array of anchoring sutures during delivery of the valve. That is, the array of anchoring sutures are pre-installed around the annulus and then threaded through corresponding locations around the sewing ring outside the body; the valve then being parachuted down the suture array to the annulus. Commissure post constriction mechanisms described herein may be incorporated into holders for such valves. It should be noted, however, that mechanical valves for the mitral position do not have such commissure posts, but could benefit from the off-axis handles described herein. Therefore, various features disclosed in the present application may be utilized independently.

The peripheral body 30 of the holder 20 as seen in FIGS. 1-7 defines a central window 50 (FIG. 1) through which the leaflets 40 of the heart valve 22 can be seen. The body 30 is illustrated as a ring with a substantially cylindrical outer edge 52 and a substantially cylindrical inner edge that defines the window 50. A plurality of solid connecting suture tabs 54 project radially outward from the outer edge 52, one for each of the commissure posts 26. In the illustrated valve there are three commissure posts 26 and three suture tabs 54.

The holder 20 connects to the prosthetic heart valve 22 via a plurality of connecting sutures or filaments 60. Each of the filaments 60 has two free ends that are connected to a tension adjustment mechanism within the holder 20 and a loop 62 that extends through the suture tabs 54, generally axially along one of the commissure posts 26, and across the outflow side of the heart valve 22, as seen in FIG. 2. More particularly, the three loops 62 mutually cross over one another at the central axis of the valve 22. Because of the crossover of the filaments 60, tension applied to each filament from the holder 20 will pull the flexible commissure posts 26 inward, thus reducing the radial profile of the combined commissure tips and reducing the chance of suture looping.

FIGS. 3-7 are a number of views of the exemplary holder 20 showing an arrangement of the valve connecting filaments 60 therein. In the illustrated embodiment, the holder 20 includes a distal base member 70 that contacts the valve sewing ring 24 as seen in FIG. 1, and a proximal cap member 72 from which the handle 32 projects. The cap member 72 couples to the base member 70 in a manner that permits relative rotation therebetween. In the illustrated embodiment, the cap member 72 includes three cantilevered legs 74 that project in a distal direction and terminate in outwardly oriented teeth 76. The legs 74 flex inward to pass through the circular opening within the base member 70 and the teeth 76 spring outward on the underside of a lower edge 78 to secure the cap member 72 to the base member 70.

Figures 3, 4:
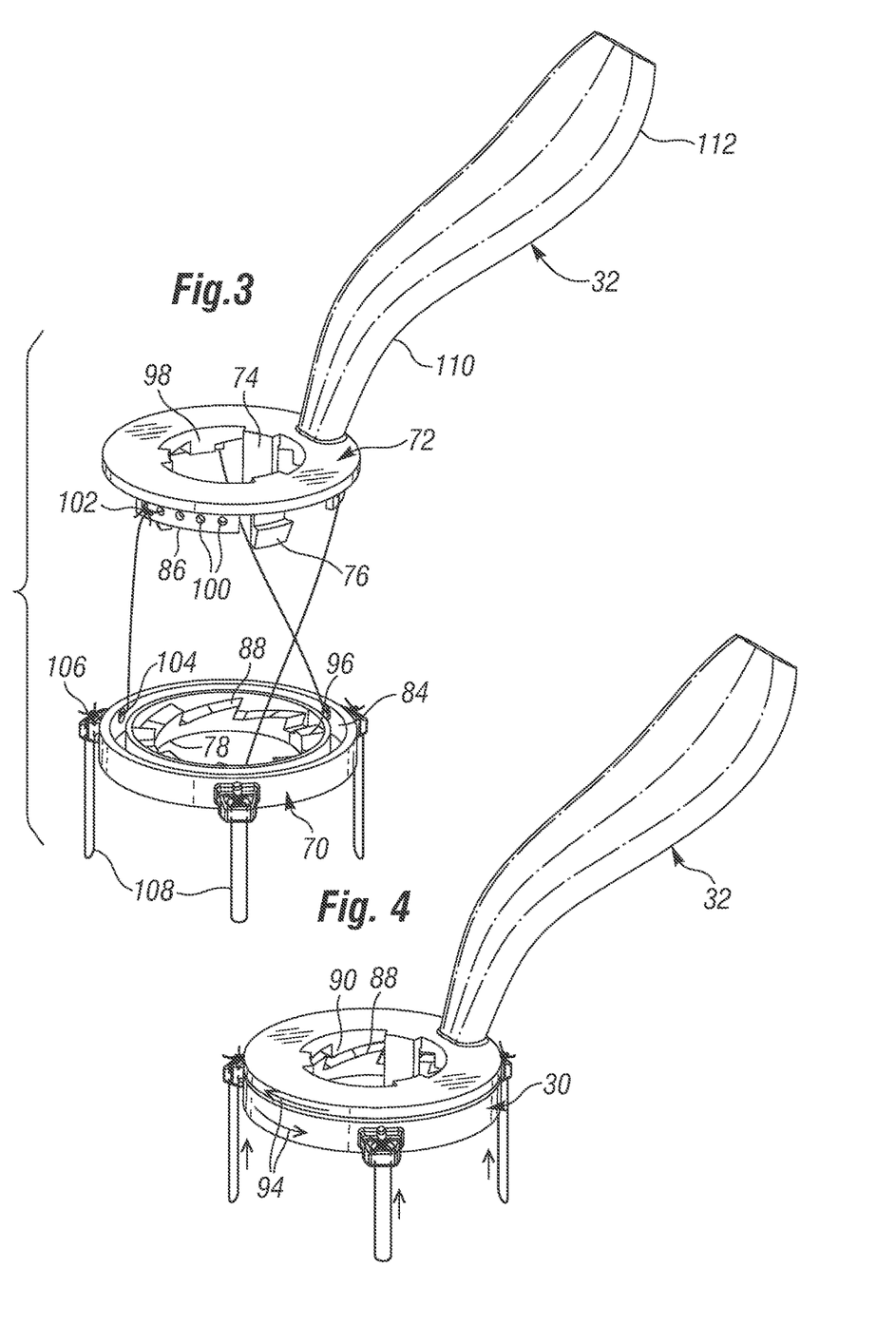
FIG. 3 is a perspective exploded view of the exemplary holder of FIG. 1 showing an arrangement of valve connecting sutures therein.
FIG. 4 is a perspective assembled view of the exemplary holder of FIG. 1 showing a step of shortening the connecting sutures.
Figure 5:
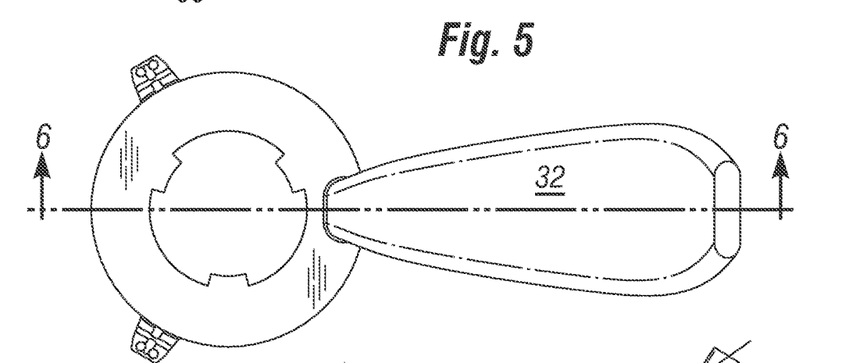
FIGS. 5-7 illustrate further details of the exemplary holder of FIG. 1.
Figure 6:
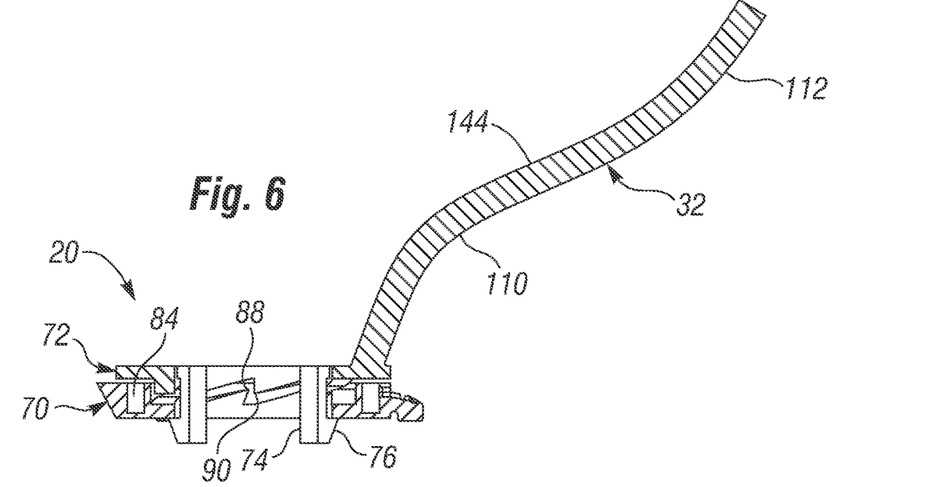

The base member 70 defines a circular channel 84 (FIG. 6) that receives a plurality of arcuate wall segments 86 (FIG. 3) extending distally from the cap member 72. The base member 70 further includes a plurality of tooth-like ramps 88 arranged in a circle inward from the circular channel 84. As seen best in FIG. 4, the cap member 72 also features a plurality of tooth-like ramps 90 arranged in a circle and aligned with the ramps 88 on the base member 70. When assembled, as shown in FIG. 4, the base member ramps 88 engage the cap member ramps 90 and provide a ratcheting mechanism that permits one-way relative rotation of the two components as shown by arrows 94, but prevent relative rotation in the opposite direction. The base member 70 further includes a step 96 (FIG. 3) that engages a like step 98 on the cap member 72 after a limited angular rotation of the cap member. In a preferred embodiment, therefore, the cap member 72 may rotate between about 20°-120° over the base member 70.

Each of the wall segments 86 seen in FIG. 3 includes a series of through holes 100 to which one free end 102 of one of the filaments 60 is tied. The filament 60 passes outward through an aperture 104 in an outer wall of the base member 70, threads through the prosthetic heart valve 22 as shown in FIGS. 1 and 2, and the other free end 106 is tied to a hole through one of the suture tabs 54. The lengths of the filaments 60 that thread through the heart valve 22 are shown in FIGS. 3 and 4 as loops 108. Rotation of the cap member 72 pulls the first free end 102 such that a portion of the filament 60 is pulled into the circular channel 84, which shortens the loops 108, as indicated in FIG. 4. The steps 96, 98 are positioned to permit a predetermined angular rotation which corresponds to a sufficient shortening of the loops 108 to correspond to pulling the commissure posts 26 inward by a desired amount.

Figure 7:
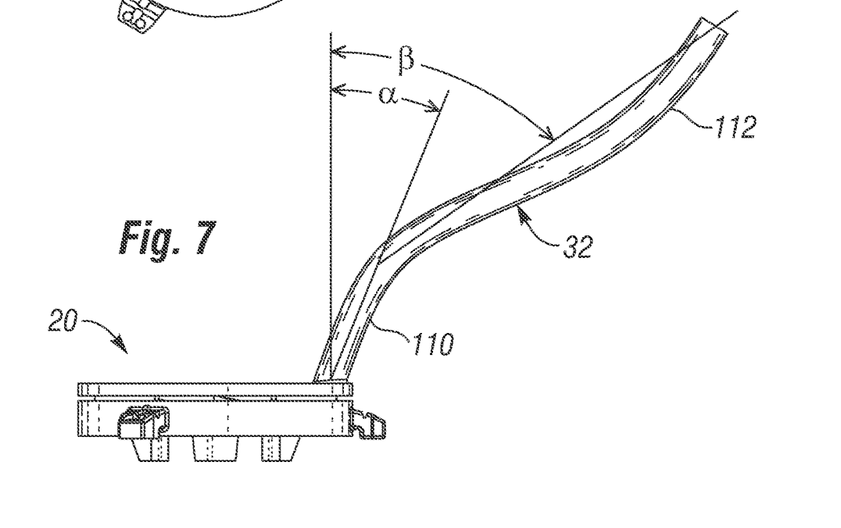

The handle 32 of the holder 20 connects to a peripheral edge of the cap member 72. As mentioned, the holder 20 features the central window 50 through which a central axis of the holder passes. Because the handle 32 connects off the central axis, and outside of the window 50, the surgeon has an unobstructed view through the center of the holder 20 to the valve 22. Moreover, the handle 32 generally angles radially outward from its connection point to the cap member 72, further enhancing visibility of both the holder 20 and the valve 22. In a preferred embodiment, handle 32 is ergonomically shaped with a first portion 110 nearest the cap member 72 that is just slightly angle radially outward, and a second portion 112 farther away from the cap member that is more sharply angled. FIG. 7 shows a first angle α from vertical (or axial) for the first portion 110, and a second angle β from vertical for the second portion 112. Desirably, the first angle α is between about 5°-20°, and the second angle β is between about 20°-60°. The handle 32 preferably has smooth curves and a point of inflection 114 (FIG. 6) between the convex first portion 110 and the concave second portion 112 (as viewed from the proximal side) to form an S-shape. Furthermore, the handle 32 is relatively narrow at its point of connection to the cap member 72, and gradually widens as it extends away. Finally, although the illustrations show the handle 112 formed as a single piece with the cap member 72, another useful embodiment is to provide a detachable handle that makes use of a quick-release mechanism well-known in the art.

A sequence of implantation of a heart valve 22 using the holder 20 begins with preparation of the prosthetic heart valve 20. Bioprosthetic heart valves are typically stored in a preservative solution, such as glutaraldehyde, and must be rinsed thoroughly before use. The valve 22 is desirably stored on the holder 20, and the ergonomic and off-axis handle 32 greatly facilitates manipulation of the valve in the operating room.

After preparation of the patient for surgery, which typically involves arresting the heartbeat, placing the patient on bypass, and opening a surgical access route, the surgeon pre-attaches a plurality of sutures around the mitral annulus. That is, sutures are passed through the annulus and tied off, commonly using pledgets (or small backing strips), and brought out through the access route in a circular array.

Next, the commissures posts 26 are biased inward by rotating the cap member 72 with respect to the base member 70. As described above, the arcuate wall segments 86 pull the first end 102 of each filament 60, thus shortening the loops 108 and creating mutual tension in the crossed-over portions of the filaments as seen in FIG. 2. The commissure posts 26 are typically angled inward by at least 10°, and more preferably by about 30°.

The anchoring sutures are then pre-threaded through the sewing ring 24 of the prosthetic heart valve 22 in the same placement as they are in the mitral annulus. Again, the ergonomic, off-axis handle 32 facilitates the step of pre-threading the sutures.

Subsequently, the surgeon uses the handle 32 to advance the prosthetic heart valve, outflow end first, along the parachute array of sutures to the mitral annulus. Once again, the advantageous off-axis and angled configuration of the handle 32 in conjunction with the central window 50 greatly assists in the delivery of the valve to the annulus. After the valve 22 has been seated in the annulus, the surgeon ties off anchoring sutures on the proximal side of the valve sewing ring 24. For this step, the handle 32 may be detached if so designed to afford better visibility and accessibility of the sewing ring 24.

Figure 8:
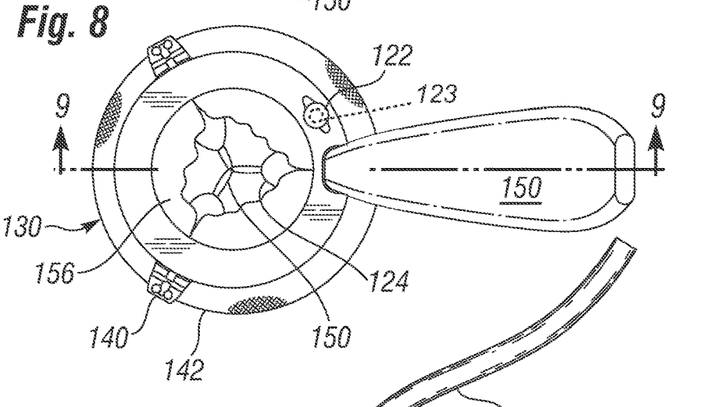
FIGS. 8-10 are elevational, plan, and sectional views of an alternative holder having a tensor for constricting the commissure posts of a prosthetic heart valve.
Figure 9:
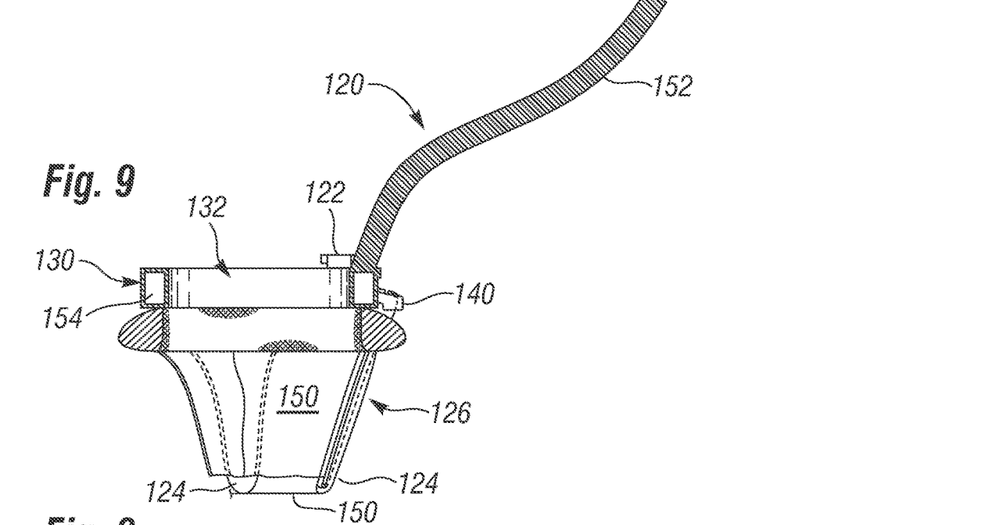
Figure 10:
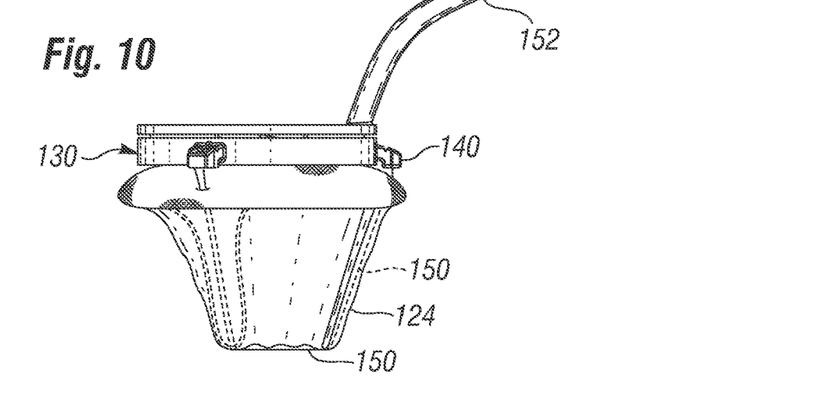

FIGS. 8-10 illustrate an alternative holder 120 having a tensor 122 for constricting commissure posts 124 of a prosthetic heart valve 126. As before, a peripheral body 130 of the holder 120 defines a central, generally circular, window 132 through which can be seen the leaflets 156 of the heart valve 126. The body 130 preferably has an annular shape with a substantially cylindrical inner edge that defines the window 132. A plurality of solid suture tabs 140 project radially outward from an outer edge 142, one for each of the commissure posts 124. In the illustrated valve there are three commissure posts 124 and three suture tabs 140.

The tensor 122 is a rotatable knob that tensions a plurality of sutures 150 that ultimately constrict the commissure posts 124. The tensor 122 may assume numerous configurations, but preferably has a size or configuration, such as the two ears as shown, that facilitates turning by the operator. The tensor 122 is desirably positioned adjacent to a handle 152 of the holder 120 that extends away from the outer edge 142. As with the earlier embodiment, the handle 152 connects to the peripheral body 130 off the central axis, and outside of the window 132, so that the surgeon has an unobstructed view through the center of the holder 120 to the valve 126. Locating the tensor 122 near the base of the handle 152 makes it more accessible and also provides good leverage while holding the handle. In an alternate embodiment, the handle 152 is attached by way of and on the axis of the tensor 122 such that rotation of the handle itself about its point of connection to the body 130 causes rotation of the tensor and thus constriction of the commissure posts. Of course, the tensor 122 could be located anywhere around the peripheral body 130.

The tensor 122 preferably rotates a spool 123 engaging a ratcheting mechanism (not shown) housed within the peripheral body 130 and around which the three constricting sutures 150 loop. The sutures 150 thread around a hollow space 154 in the body 130 to passages leading out to the three suture tabs 140. As described above, each constricting suture 150 includes a loop that extends from guides in a suture tab 140 and through one of the commissure posts 124. From the tips of the commissure posts 124, as seen in FIG. 8, the loops of sutures 150 mutually cross over one another at the central axis of the valve 126. The tips of the commissure posts 124 are shown constricted inward by virtue of applying tension to the sutures 150 via the tensor 122. The ratcheting mechanism maintains the tension.

Flexible valve leaflets 156 are shown spread apart looking through the holder 120 in FIG. 8, which is possible to do manually by the surgeon because of the large central window 132. The surgeon can view the approaching annulus during valve delivery, as well as during the process of properly seating and orienting the valve in the annulus. The window 132 allows for full visualization of the valve and commissures 124, so that if suture looping during delivery has occurred it is more visible. Preferably, the window 132 has a diameter of as great as or slightly less than the valve orifice, and is sized to correspond to the valve size. Prosthetic valves are typically provided with nominal flow orifice sizes between 25-33 mm, in 2 mm increments, corresponding to a labeled size. Consequently, the window 132 preferably has a diameter of between about 25-33 mm, depending on the valve size.

While the invention has been described in its preferred embodiments, it is to be understood that the words which have been used are words of description and not of limitation. Therefore, changes may be made within the appended claims without departing from the true scope of the invention.

What is claimed is:

1. A combination including a holder for handling and delivering a prosthetic mitral heart valve to an implantation site, comprising:
   a prosthetic mitral heart valve having an inflow end and three flexible commissure posts ending in tips projecting in an outflow direction;
   a holder body contacting the inflow end of the heart valve, the holder body defining a central window aligned along an inflow-outflow axis through which leaflets of the heart valve are visible and having at least one peripherally-extending internal passage extending around the central window, wherein the holder body has relatively rotatable rings; and
   three connecting sutures each fixed to the holder body and having a loop extending at least partly around the peripherally-extending internal passage, out of the holder body and along each of the commissure posts of the heart valve, the three loops of the connecting sutures mutually crossing over between the tips of the commissure posts, wherein each connecting suture has two free ends attached to different rotatable rings of the holder body, and wherein relative rotation of the rings applies tension to the connecting suture loops and causes the commissure post tips to move radially inward.

2. The combination of claim 1, wherein the relatively rotatable rings have engaging ratchet teeth to permit relative rotation in one direction only, and a pair of steps that engage to limit total relative rotation.

3. The combination of claim 1, wherein the holder further includes an off-axis handle attached to one of the rotatable rings of the holder body facing away from the heart valve.

4. The combination of claim 3, wherein the handle attaches immediately adjacent a peripheral edge of the holder and angles radially outward therefrom.

5. The combination of claim 4, wherein the handle angles outward in an S-shape with a first portion nearest the peripheral edge of the holder that is just slightly angled radially outward and a second portion farther away from the peripheral edge that is more sharply angled.

6. The combination of claim 4, wherein the handle has a first portion nearest the peripheral edge of the holder that angles outward between 5°-20° and has a second portion farther away from the peripheral edge angled outward between about 20°-60°.

7. The combination of claim 4, wherein the handle is made of a non-metallic material.

8. The combination of claim 3, wherein the off-axis handle is relatively narrow at its point of attachment to the rotatable ring of the holder body, and gradually widens as it extends away.

9. A combination including a holder for handling and delivering a prosthetic mitral heart valve to an implantation site, comprising:
   a prosthetic mitral heart valve having an inflow end and three flexible commissure posts ending in tips projecting in an outflow direction;
   a holder body contacting the inflow end of the heart valve, the holder body defining a central window aligned along an inflow-outflow axis through which leaflets of the heart valve are visible, wherein the holder body has relatively rotatable rings rotatable with respect to each other about the axis;
   connecting sutures each fixed to the holder body and extending from the holder body along each of the commissure posts of the heart valve, the connecting sutures crossing between the tips of the commissure posts, wherein each connecting suture has two free ends attached to different rotatable rings and a loop that extends from the holder body through the heart valve and across the tips of the commissure posts, and wherein relative rotation of the rings applies tension to the connecting sutures and causes the commissure post tips to move radially inward; and
   an off-axis handle attached to a side of the holder body facing away from the heart valve immediately adjacent a peripheral edge of the holder and angling radially outward therefrom.

10. The combination of claim 9, wherein the relatively rotatable rings have engaging ratchet teeth to permit relative rotation in one direction only, and a pair of steps that engage to limit total relative rotation.

11. The combination of claim 9, wherein the off-axis handle attaches to one of the rotatable rings of the holder body facing away from the heart valve.

12. The combination of claim 9, wherein the handle angles outward in an S-shape with a first portion nearest the peripheral edge of the holder that is just slightly angled radially outward and a second portion farther away from the peripheral edge that is more sharply angled.

13. The combination of claim 12, wherein the first portion angles outward between 5°-20° and the second portion is angled outward between about 20°-60°.

14. The combination of claim 9, wherein the handle is made of a non-metallic material.

15. The combination of claim 14, wherein the handle is molded of polypropylene.

16. The combination of claim 9, wherein the off-axis handle is relatively narrow at its point of attachment to the side of the holder body, and gradually widens as it extends away.

17. A combination including a holder for handling and delivering a prosthetic mitral heart valve to an implantation site, comprising:
   a prosthetic mitral heart valve having an inflow end and three flexible commissure posts ending in tips projecting in an outflow direction, the heart valve defining a flow orifice having a nominal size in millimeters corresponding to a labeled size;
   a holder body contacting the inflow end of the heart valve, the holder body defining a large central window aligned along an inflow-outflow axis through which leaflets of the heart valve are visible, the central window having a diameter approximately the same as the heart valve size, wherein the holder body has relatively rotatable rings rotatable with respect to each other about the axis;
   connecting sutures each fixed to the holder body and connecting the heart valve to the holder, and each connecting suture has two free ends attached to different rotatable rings and a loop therebetween that passes through the valve and across the commissure post tips, wherein relative rotation of the rings applies tension to the connecting sutures and causes the commissure post tips to move radially inward; and
   an off-axis handle attached to a side of the holder body facing away from the heart valve immediately adjacent a peripheral edge of the holder and angling radially outward therefrom.

18. The combination of claim 17, wherein the relatively rotatable rings have engaging ratchet teeth to permit relative rotation in one direction only, and a pair of steps that engage to limit total relative rotation.

19. The combination of claim 17, wherein the off-axis handle attaches to one of the rotatable rings of the holder body facing away from the heart valve.

20. The combination of claim 17, wherein the off-axis handle angles outward in an S-shape with a first portion nearest the peripheral edge of the holder that is just slightly angled radially outward and a second portion farther away from the peripheral edge that is more sharply angled.

21. The combination of claim 20, wherein the first portion angles outward between 5°-20° and the second portion is angled outward between about 20°-60°.

22. The combination of claim 20, wherein the handle is made of a non-metallic material.

23. The combination of claim 17, wherein the off-axis handle is relatively narrow at its point of attachment to the side of the holder body, and gradually widens as it extends away.

* * * * *